United States Patent
Somers

(10) Patent No.: US 6,342,045 B1
(45) Date of Patent: Jan. 29, 2002

(54) SAFETY SYRINGE

(76) Inventor: Brice Somers, 1, chemin de la Sapinière, 1253 Vandoeuvres (CH)

(*) Notice: Subject to any disclaimer, the term of this patent is extended or adjusted under 35 U.S.C. 154(b) by 0 days.

(21) Appl. No.: 09/424,531
(22) PCT Filed: May 20, 1998
(86) PCT No.: PCT/IB98/00774
§ 371 Date: Nov. 24, 1999
§ 102(e) Date: Nov. 24, 1999
(87) PCT Pub. No.: WO98/53867
PCT Pub. Date: Dec. 3, 1998

(30) Foreign Application Priority Data

May 26, 1997 (CH) .................................. 1240/97
Dec. 9, 1997 (CH) .................................. 2834/97

(51) Int. Cl.[7] ............................................. A61M 5/00
(52) U.S. Cl. ....................... 604/110; 604/187; 604/218; 604/198; 604/243
(58) Field of Search ............................. 604/110, 187, 604/164.01, 181, 192, 195, 198, 197, 213, 218, 221, 222, 225, 228, 229, 235, 236, 240, 241, 243, 263; 128/919; 222/386

(56) References Cited

U.S. PATENT DOCUMENTS

| 4,507,177 A | 3/1985 | Duckworth et al. | |
|---|---|---|---|
| 4,675,005 A | 6/1987 | Deluccia | |
| 4,935,016 A | * 6/1990 | Deleo | 604/198 |
| 5,098,390 A | * 3/1992 | Wallingford | 604/195 |
| 5,152,750 A | 10/1992 | Haining | |
| 5,167,640 A | * 12/1992 | Balding | 604/192 |
| 5,219,338 A | * 6/1993 | Haworth | 664/198 |
| 5,256,151 A | * 10/1993 | Chul | 604/195 |
| 5,342,308 A | * 8/1994 | Boschetti | 604/110 |
| 5,368,568 A | * 11/1994 | Pitts et al. | 604/110 |
| 5,405,327 A | 4/1995 | Chen | |
| 5,531,705 A | * 7/1996 | Alter et al. | 604/195 |
| 5,569,203 A | 10/1996 | Chen | |

FOREIGN PATENT DOCUMENTS

| EP | 0 326 983 | 8/1989 |
|---|---|---|
| EP | 0 347 742 | 12/1989 |
| EP | 0 557 511 | 9/1993 |
| WO | WO 90/06148 | 6/1990 |
| WO | WO 93/10842 | 6/1993 |
| WO | WO 94/05356 | 3/1994 |
| WO | WO 97/10867 | 3/1997 |

* cited by examiner

Primary Examiner—Richard K. Seidel
Assistant Examiner—Cris Rodriguez
(74) Attorney, Agent, or Firm—Young & Thompson

(57) ABSTRACT

A safety syringe includes a barrel, a needle-carrier and a plunger. The plunger and the needle-carrier each have a coupling system which connects them by a simple axial push of the plunger. The distal part of the barrel has an internal annular stop. The central part of the needle-carrier has an external diameter corresponding to the internal diameter of the annular stop while the proximal extremity of this part of the needle-carrier has a diameter corresponding to the internal diameter of the distal part of the barrel. Elements are provided to prevent temporarily the needle-carrier from being pushed inside the barrel through axial pressure against the distal tip of the needle-carrier.

14 Claims, 3 Drawing Sheets

FIG. 3
FIG. 4
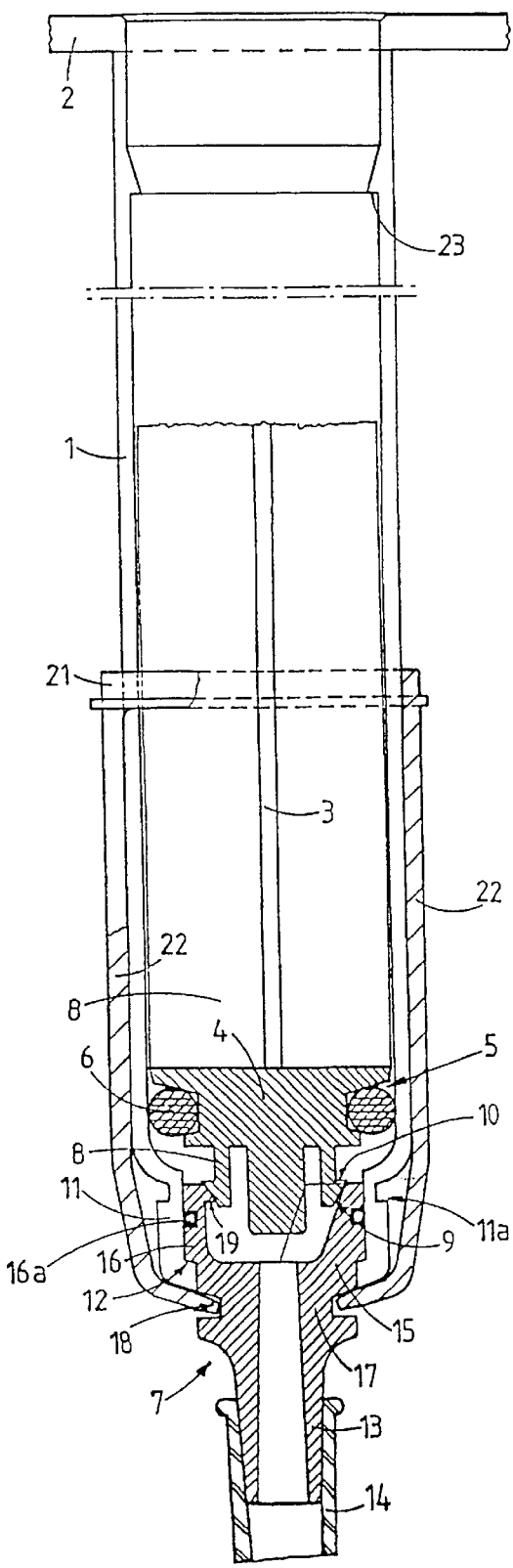
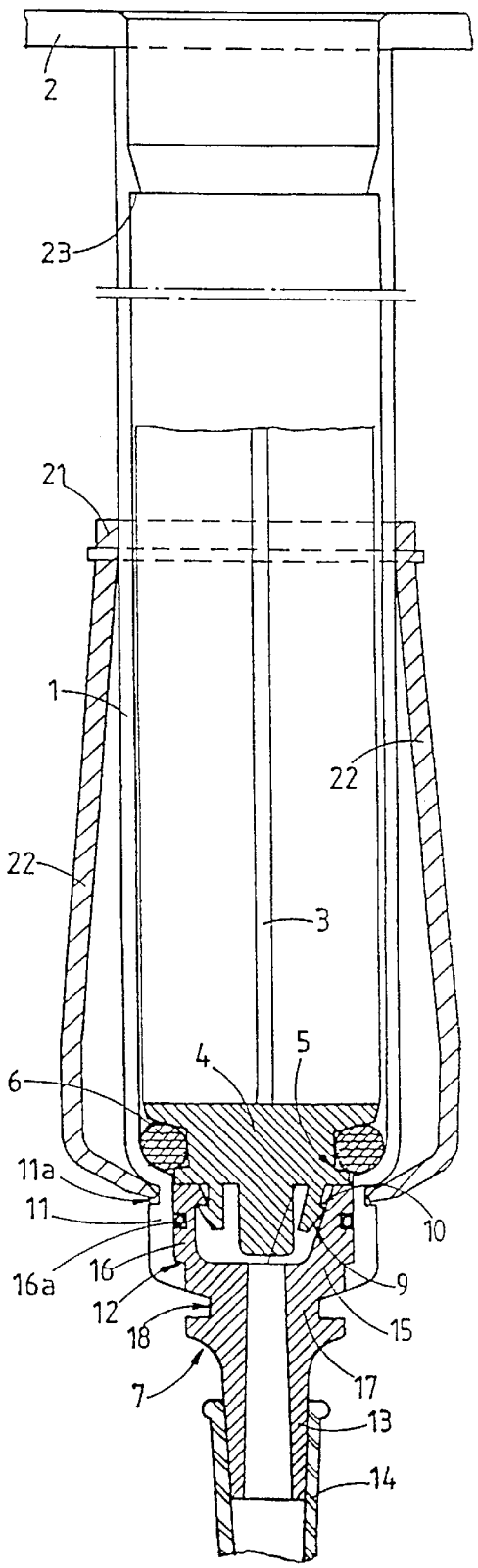

SAFETY SYRINGE

CROSS REFERENCE TO RELATED APPLICATION

This is the 35 USC 371 national stage of International application PCT/IB98/00774 filed on May 20, 1998, which designated the United States of America.

FIELD OF THE INVENTION

The present invention concerns safety syringes for medical uses which permit the limitation and if possible the avoidance of injury to healthcare workers. The aim of these safety syringes is evidently to avoid risk of contamination during handling of the syringe and to prevent the needle, after administering an injection into a patient suffering from an illness such as viral hepatatis or AIDS, from injuring the nurse before the needle has been safely protected

BACKGROUND OF THE INVENTION

Such safety syringes are known in documents WO 90/06148, EP 0.326.983, EP 0.347.742, U.S. Pat. No. 4,507,177 or U.S. Pat. No. 4,675,005. All of the syringes described in these documents necessitate the retracting of the needle into the syringe barrel after use, but by complicated manipulations involving rotary movements, coupling by bayonet etc. which are impractical movements which hospital personnel are not used to carrying out and which require the use of two hands, one of which can approach the sharp tip of an infected needle.

SUMMARY OF THE INVENTION

The aim of the present invention is to create a safety syringe for medical use permitting the needle to be retracted inside the cylinder after use but which can be utilized in the same way as all standard syringes for its preparation and use, that is to say fixing the required needle, filling, changing needle if necessary, coupling onto an air filter if necessary, evacuation of air-bubbles and injection. Nevertheless, the difference and the advantage compared to standard syringes is that the operator's hands cannot approach the dangerous distal zone of the syringe which is a source of injury because it is obligatory that the active hand which pulls the piston is occupied at the proximal extremity of the syringe.

Another aim of the invention is to prevent the user to try to re-cap the infected needle or to have to dispose of this needle in a specialized disposal box which is not always handy. Yet another aim is to facilitate the reading of the volume of liquid introduced through the needle.

Another aim of the present invention is the creation of a purely mechanical syringe having a small number of parts, easy to manufacture and at low cost compared to other known safety syringes, and with a cost comparable to existing low-cost standard single-use syringes.

Another aim of the present invention is the creation of a safety syringe which allows the user, before employing the syringe, to choose the appropriate standard needle and to fix it onto the syringe the same as with low-cost conventional single use syringes, which is often not possible with safety syringes.

The objective of the present invention is a safety syringe which avoids the disadvantages of existing syringes permitting the above mentioned aims to be reached, comprising a barrel, a plunger which can be moved linearly and remain watertight and a needle carrier similarly movable linearly inside the barrel and which distinguishes itself by the characteristics listed in claim 1.

BRIEF DESCRIPTION OF THE DRAWINGS

The annexed drawings show schematically and as an example a form of execution and variant of the safety syringes according to the invention.

FIG. 3 illustrates the coupling of the needle carrier onto the plunger.

FIG. 4 illustrates a longitudinal section of the syringe at the end of its stroke, the cursor having been slid back to allow the needle carrier to be retracted with its needle inside the cylinder.

DETAILED DESCRIPTION OF THE INVENTION

Figure 1:
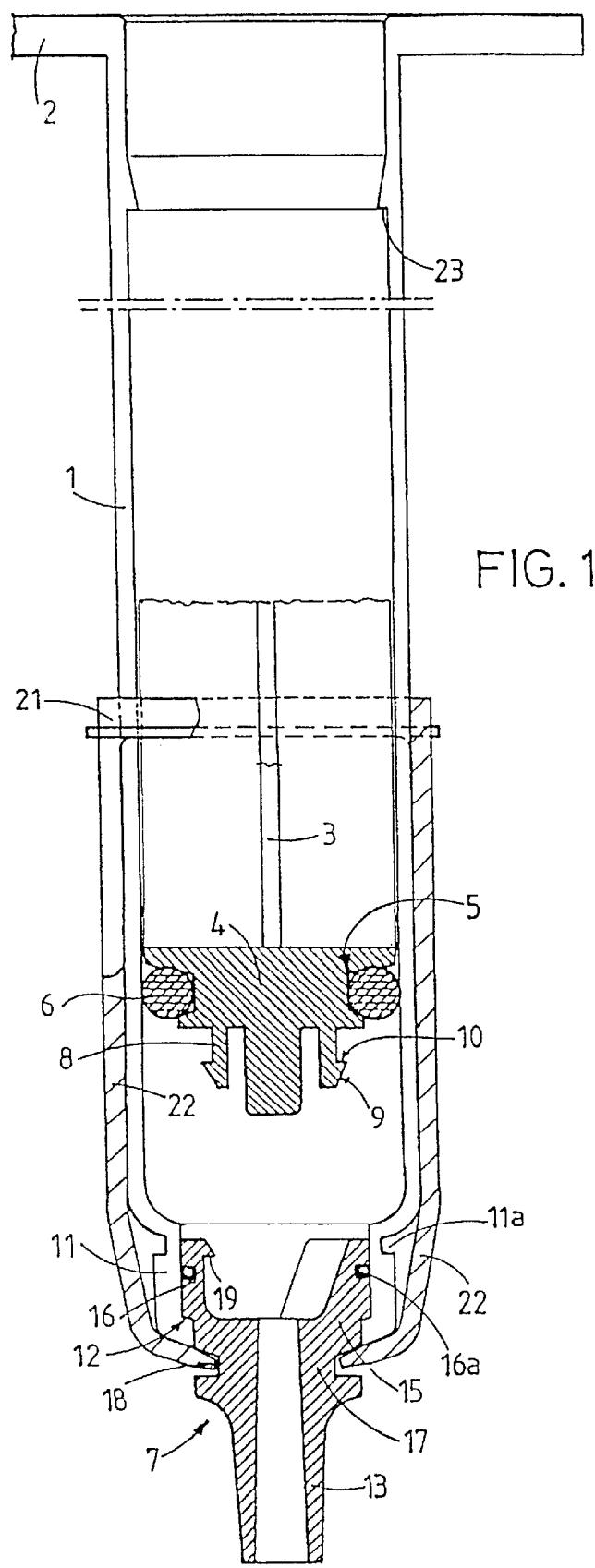
FIG. 1 illustrates a longitidunal section of the syringe according to the invention in its position before use, during storage.
Figure 2:
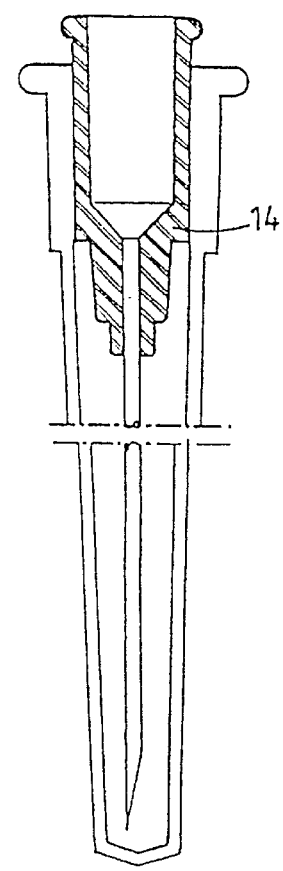
FIG. 2 illustrates a longitudinal section of a standard needle in its protection cap, intended to be fixed onto the distal end of the needle carrier by push-fit.

The safety syringe illustrated particularly in FIG. 1 constitutes a barrel 1 moulded by injection of, for example, transparent polypropylene. This barrel 1 has a length and a diameter which depend on the capacity of the syringe, of its ease of use and other normal features such as the length of the standard needles.

This barrel 1 of the syringe has at its proximal extremity a flange 2 moulded integrally with the barrel, but of a larger diameter or having a lengthened shape in plan view.

The syringe consists further of a plunger having a shaft 3 of which the proximal extremity which emerges out of the barrel 1 has a push-button. The plunger head 4 situated at the distal extremity of shaft 3 includes a housing 5 to hold an O-ring 6 which slides in a watertight fashion within the barrel 1.

The use of an O-ring to ensure the watertightness between the plunger and the barrel is advantageous because this type of joint costs less than a full piston head moulded in rubber; furthermore it can be injection moulded in a synthetic elastomer which meets all medical requirements.

The distal extremity of the shaft 3 situated beyond the O-ring 6 of the plunger in the direction of the distal extremity of barrel 1 consists of the male organs 8 of a coupling system of the plunger 3–6 with a needle carrier 7. These male coupling organs are formed by projections 8 extending axially in the direction of the distal extremity of the barrel 1, these projections 8 being situated around a circumference centred on the axis of barrel 1 and of which the radial extension is in the order of 40° to 120° according to the number of the projections 8. Generally one uses three or four projections 8 uniformly distributed around the axis of plunger 3–6 and presenting an angular spread included between 45° and 70°. Each of the projections 8 has at its tip an inclined plane 9 on its external face widening in the direction of the proximal extremity of barrel 1 and forming a retaining ridge 10 on the cylindrical face of the proximal extremity of projection 8. The distal part 11 of barrel 1 presents a smaller diameter extension with an annular internal stop 12 at its distal extremity formed by a circular brim facing towards the axis of barrel 1 so as to reduce the distal opening of barrel 1. This distal part 11 of the barrel has an annular groove 11a situated on its external peripheral surface.

The syringe also includes a needle carrier 7 comprising a distal end consisting of a hollow cone 13 designed to hold an hypodermic needle 14 by push-fit. The proximal end 15 of the needle carrier comprises a cylindrical portion 16 having an external diameter which corresponds of the internal diameter of the distal extension 11 of barrel 1. This proximal extremity 16 of the needle-carrier 7 slides in a watertight manner inside the distal part of the barrel.

A seal, for example an O-ring, 16a lodged in an annular channel around the needle-carrier ensures a perfectly watertight fit between the barrel 1 and the needle-carrier 7. It is possible to retract the needle-carrier into barrel 1 when it has been freed by sliding the cursor 21, 22. The external diameter of the distal part of needle-carrier 7 does not exceed the diameter of the distal opening of barrel 1.

The median section 17 of this needle-carrier presents a diameter which corresponds to the internal diameter of the brim situated at the distal extremity 11 of the barrel. Thus the furthest distal position of the needle-carrier 7 in the barrel 1 is defined by the contact of the shoulder separating the proximal part 16 of the median section 17 of the needle-carrier 7 with the stop 12 of barrel 1.

This median section 17 of needle-carrier 7 has a circular groove 18 with a proximal annular face situated, when the needle-carrier 7 is in its furthest distal position, in the extension of the frontal face of the rim of the distal extremity 11 of barrel 1.

In the standby or storage position of the syringe illustrated in FIG. 1, the needle-carrier 7 is lodged in the distal part 11 of barrel 1.

On part of its internal circumference, about 60° to 120°, the proximal portion 16 of the needle-carrier 8 includes a ridge or catch 19 which constitutes the female part of the coupling of the plunger into the needle-carrier intended to cooperate, as we shall see later, with the catch 10 of the tip of at least one of the fingers 8 of the plunger.

The coupling comprised by the catches 10 of one or two fingers 8 and the catch 19 of the needle-carrier 7 is unlockable. It thus possible to re-lock together the plunger and the needle-carrier after these have already been locked together once, and the needle can then still be pulled inside the barrel 1 after use as soon as the user has slid back the cursor 22 and thus freed the needle-carrier 7.

In its initial position during storage (FIG. 1) an operator can push-fit a needle 14 onto the distal projection 13 of the needle-carrier 7 and also change the needle as required, in the same way as is done with conventual syringes. The needle carrier 7 is locked in this position in relation to the barrel 1 by a cursor. This cursor consists of a ring 21–22 sliding freely around the barrel. This ring 21 has at least one flexible locking finger 22 extending in the direction of the distal tip of the barrel 1. In its operational position (FIG. 1), the cursor is in its distal position and the ends of its fingers 22 are lodged in groove 18 of the needle-carrier 7. Thus the needle-carrier 7 is locked in its service position and cannot be pulled out or pushed into the barrel for example during needle fixing, aspiring a liquid from a bottle or administering an injection.

This cursor is transparent and in no way interferes with visibility when filling the syringe.

The operator can then carry out all necessary clinical requirements; aspire a liquid and inject it into a patient, or sample blood from a patient's vein and empty it into a test tube using traditional manipulations.

When the operator has finished and wishes to dispose of the syringe, the operator must never cap the needle nor discard the naked needle, which always presents a great potential danger of needlestick injury, but at the end of the injection stroke a slightly firmer pressure is applied to the plunger thus causing the coupling together of the plunger and the needle-carrier, the catch 10 of fingers 8 locking by elastic deformation of the fingers 8 onto the catch 19 of the needle-carrier 7 as shown in FIG. 4.

As long as the cursor 21–22 remains in its distal service position, the plunger 4 can still be unlocked from the needle-carrier 7. This is important because this coupling at the end of the distal stroke of the plunger can sometimes happen unintentionally.

Before pulling the needle-carrier 7 inside the barrel 1 by means of the plunger, the user must unlock the needle-carrier 7 by sliding the cursor 21–22 in a proximal direction along barrel 1 which pulls the fingers 22 out of the groove 18 of the needle-carrier 7, which fingers 22 can then be parked in the annular external depression 11a around the barrel.

Figure 5:
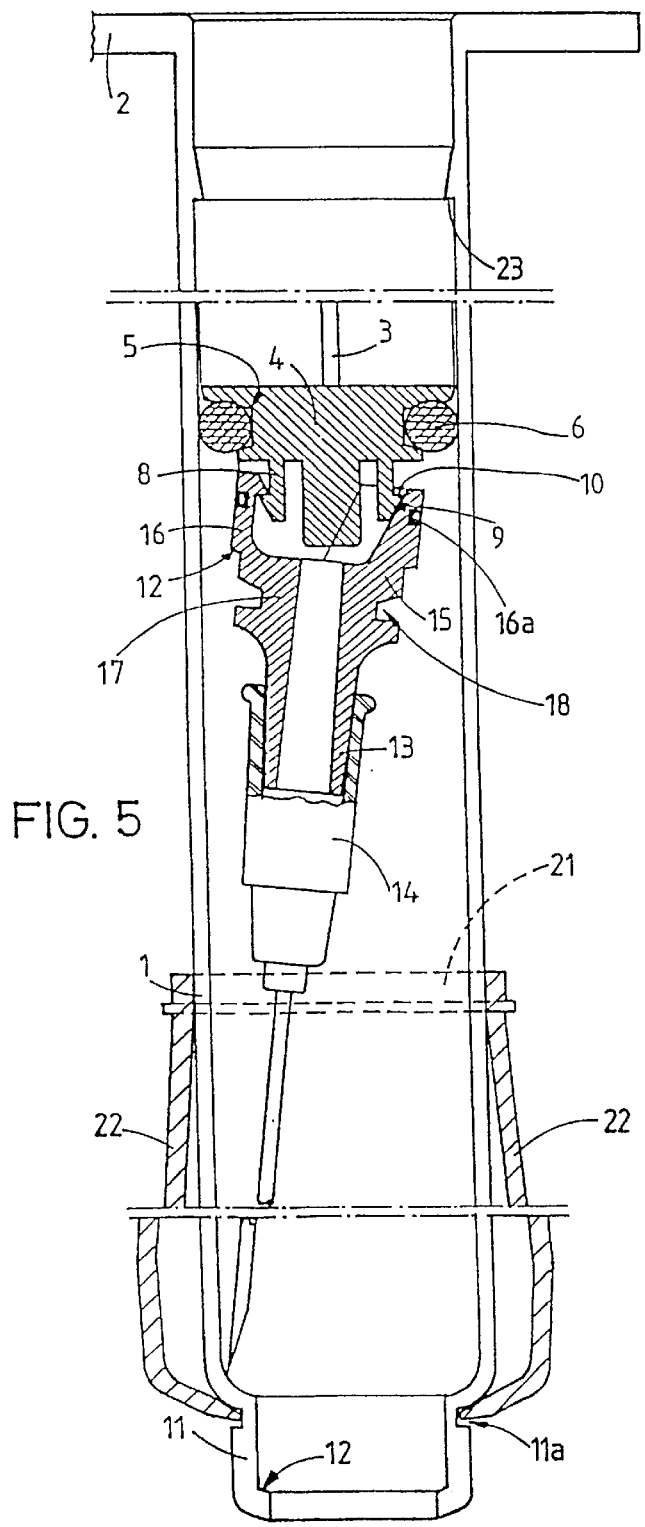
FIG. 5 illustrates the needle carrier and its needle retracted inside the barrel.

From this moment, the plunger and the needle-carrier are coupled together and, after having slid back the cursor 21–22 to free the needle-carrier, in withdrawing the plunger one withdraws the needle-carrier 7 and its needle 14 inside the barrel 1 (FIG. 5).

Because of the flexibility of the fingers 8 and that only one or two of these are coupled with catch 19 of the needle carrier 7, this latter is inclined in relation to the axis of the barrel (FIG. 5) so that when the plunger has been sufficiently retracted, the needle can no longer emerge from the barrel.

The proximal extremity of the barrel 1 contains an internal stop ring 23 with an inclined ramp which allows the plunger to be inserted into the barrel 1 but which stop ring blocks its being pulled out. Thus, the operator cannot pull the needle out of the barrel through its proximal opening and the used needle is irrevocably interred inside the barrel 1. This stop ring is considerably more prominent than the stop rings normally included in standard syringes where the plunger can easily be removed from the barrel through its proximal opening.

In a variant, the plunger shaft can have a Y-section instead of an X-section. This can provide an economy of around 25% of plastic used for this part while still providing it with sufficient rigidity. By this means the manufacturing cost of these syringes can be reduced.

The principal advantages of this safety syringe are:
1. It will eliminate any possibility for healthcare personnel to suffer accidental needlestick injury with an infected needle, after having administered an injection.
2. It's mode of use (filling/injection) remains exactly the same as the existing procedure for use with standard syringes.
3. To render it totally non-reusable, it is merely necessary to push the plunger to the limit of its stroke, which couples the distal tip of the plunger into the needle carrier. The needle is then withdrawn by the plunger, after the cursor has been slid back, inside the barrel where it is blocked.
4. The needle having by these actions been inclined and pressed against the interior of the barrel, it cannot by any means re-emerge through the distal opening of the barrel. Because of the stop ring 23, it furthermore cannot be pulled out of the barrel through the proximal opening.
5. During the push-fitting of a needle onto the needle carrier and during the entire cycle of use of the syringe, it is impossible to push the needle carrier inside the the barrel, as it is locked by the cursor 21,22.

6. On the other hand, the coupling with the needle carrier by the plunger (see 3 above) presents no difficulty.
7. The syringe cannot be reused and can be discarded for incineration without the slightest danger.
8. Neither hand can approach the dangerous distal zone which can cause needlestick accidents. One hand is holding the syringe by its barrel while the other hand is pulling the plunger.
9. It consists of four moulded plastic components, plus two standard elastomeric seals.
10. It accepts all standard needles and all volumes of the syringe incorporate the same sized needle carrier.
11. The manufacturing costs are comparable to those of a standard non-safety single use syringe.
12. The dead volume at the end of an injection is within the ISO international standards.

Figure 6:
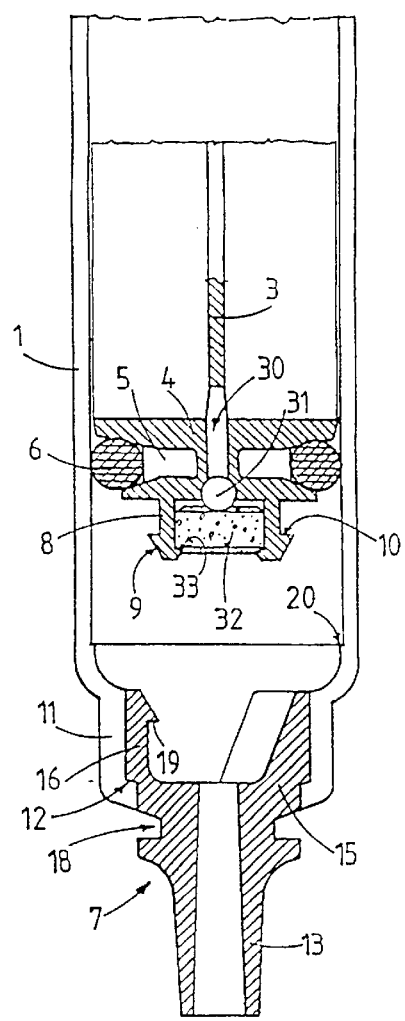
FIG. 6 illustrates a variant of the distal extremity of the syringe, particularly of the plunger, rendering the syringe automatically non-reusable after a single use.

FIG. 6 illustres a form of execution of the syringe which is self-destructing, in other words once it has been used it can no longer be used, even intentionally.

To realise this, the distal tip of the plunger shaft has a passage 30 connecting the spaces on barrel 1 situated each side of the watertight seal 6 of the plunger.

This passage 30 is blocked and rendered watertight by a blocking means, for example a ball 31, preferably elastomeric, held in position by an element 32 lodged and held between the fingers 8 which carry internal rims 33 for this purpose. This element 32 has the characteristic of having a variable resistance to compression depending on whether it is dry or wet. In its dry state it is hard and presses the ball 31 strongly against its seating, thus blocking the passage 30.

As soon as the syringe has been filled with the liquid the element 32 has its mechanical resistance diminished. Thus, while the user empties the liquid contained in the syringe, ball 31 is constantly pressed against its seating, the pressure applying in the distal chamber of barrel 1 being greater than that applying in the proximal chamber of said barrel.

On the other hand, if the user wishes to refill the syringe he must, to aspire the liquid through the needle, pull back the plunger which causes a depression in the distal chamber of the barrel. At this moment, ball 31 moves by deforming element 32 which is now soft and it is air that fills the distal chamber of the barrel, which is now unable to be filled with a liquid.

It is evident that in this second form of execution the user can equally well push the plunger to the limit of its stroke in the barrel and to definitely couple this to the needle-carrier then pull the needle-carrier and the needle it is carrying inside the barrel so as to then discard the syringe in perfect safety.

Thus, this variant, in addition to the advantages of the first version of the syringe that has been described, is self-destructing; it cannot be re-used, even intentionally.

In another variant and with the aim of reducing even more the amount of plastic required for manufacture of the syringe, it is possible to mould the finger-grip flange 2, not at the proximal extremity of the barrel 1 but at a distance of 1 to 2 cm from this proximal extremity of the barrel. In so doing, it is thus possible to shorten the length of the plunger shaft 3, advancing the position of its push-button (2) to abut, when the plunger head 4 has been pushed to the limit of its stroke inside the barrel, against the opening of the barrel at its proximal extremity, without affecting the ease of manipulation of the plunger.

What is claimed is:

1. A safety syringe for medical use comprising:

a barrel having a distal part and a proximal part;

a needle-carrier sliding in a watertight fashion in the distal part of the barrel;

a plunger having a shaft and sliding in a watertight fashion in the proximal part of the barrel;

the plunger and the needle-carrier each comprising a coupling organ interconnecting by a simple axial push on the plunger to enable the needle-carrier with its needle to be withdrawn inside the barrel after injection;

the distal part of the barrel having an internal annular stop which prevents the needle-carrier from being pulled or pushed out of the barrel through its distal opening;

a central part of the needle-carrier having an external diameter greater than the internal diameter of the annular stop;

a proximal part of the needle-carrier having a diameter corresponding to the internal diameter of the distal part of the barrel;

manually operated control means slidably mounted on the barrel and comprising locking members, displaceable from a forward locking position where said members positively lock the needle-carrier in its forward-most distal position in the barrel and prevents said needle-carrier from being pushed inside the barrel due to an axial pressure applied to a distal end of the needle-carrier, or from being withdrawn inside the barrel by the plunger to a retracted unlocked position after the locking members are disengaged from the needle-carrier, which is then free to be pulled or withdrawn inside the barrel.

2. The syringe according to claim 1, wherein the manually operable control means comprise a cursor formed by a ring sliding freely around the barrel and including at least one flexible locking finger having a tip which lodges, when in its forward locking position, in a groove of the needle-carrier.

3. The syringe according to claim 2, wherein the barrel has an annular groove around its distal part for parking the fingers of the cursor when in a slid-back position to free the needle-carrier.

4. The syringe according to claim 1, wherein the coupling organ comprises a catch covering only one part only of a tronconical internal surface of the proximal part of the needle-carrier, while a member of the plunger which couples the plunger to the needle-carrier comprises at least three fingers fixed to the shaft of the plunger advancing axially in the direction of the distal extremity of the barrel; said fingers comprising ends having an external conical surface and a hooking ridge designed to cooperate with a conical wall of the needle-carrier and the catch by elastic deformation of said fingers upon pushing the plunger against the needle-carrier.

5. The syringe according to claim 4, wherein the catch and the needle-carrier do not occupy the entire periphery of the internal conical surface of the proximal part of the needle-carrier so that due to the elasticity of the fingers of the plunger, the needle-carrier takes up an oblique position, inclined in relation to the axis of the syringe when said needle-carrier is withdrawn inside the barrel.

6. The syringe according to claim 5, wherein the internal annular stop is formed by a rim facing in the direction of the axis of the syringe which reduces the diameter of the distal opening of the barrel.

7. The syringe according to claim 1, wherein the plunger comprises a head provided with a groove in which a seal is positioned sliding in a watertight fashion against the inner wall of the barrel.

8. The syringe according to claim 1, wherein the proximal extremity of the barrel comprises a stop ring formed by an internal annular projection of the barrel wall; said projection presenting a conical part decreasing in the direction of the proximal end of the barrel and an annular face in the direction of the distal part of the barrel; said stop ring preventing the plunger from being withdrawn from the barrel through its proximal opening.

9. The syringe according to claim 1, wherein the central part of the needle-carrier comprises an annular groove.

10. The syringe according to claim 1, wherein the external surface of the proximal part of the needle-carrier has a groove in which is housed a circular seal.

11. The syringe according to claim 1, wherein the shaft of the plunger has a general shape of a Y.

12. The syringe according to claim 1, wherein the distal tip of the plunger has a passage connecting distal and proximal chambers of the barrel separated by said plunger; an element of variable resistance held between the fingers for holding means of blocking said passage; said element having a mechanical resistance which is lower when wet than when dry.

13. The syringe according to claim 1, wherein the barrel comprises a finger-grip collar positioned at a distance of between 1 to 2 cm from the proximal extremity of the barrel.

14. The syringe according to claim 1, wherein the coupling of the plunger into the needle-carrier is unlockable by a simple axial pulling.

* * * * *